US005463173A

United States Patent [19]
Hoffbeck

[11] Patent Number: 5,463,173
[45] Date of Patent: Oct. 31, 1995

[54] INBRED CORN LINE PHR61

[75] Inventor: Loren J. Hoffbeck, Tipton, Ind.

[73] Assignee: Pioneer Hi-Bred International, Inc., Des Moines, Iowa

[21] Appl. No.: 164,586

[22] Filed: Dec. 9, 1993

Related U.S. Application Data

[63] Continuation-in-part of Ser. No. 649,800, Feb. 1, 1991, abandoned.

[51] Int. Cl.$^6$ .............................. A01H 5/00; A01H 1/00; C12N 5/04
[52] U.S. Cl. ................. 800/200; 800/250; 800/DIG. 56; 47/58; 435/240.4; 435/240.49; 435/240.50
[58] Field of Search ..................................... 800/200, 205, 800/DIG. 56; 47/58, 58.03, 58.05; 435/240.4, 145.49

OTHER PUBLICATIONS

Wych (1988) In Corn & Corn Improvement. Editor 6, F. Sprague et al. pp. 565–607 ASA pub 183rd Edition.
Hallauer et al. (1988) IB1D pp. 463–564.

Meghji et al. (1984) Crop Science vol. 24, pp. 545–549.
Poehlmen (1987) *Breeding Field Crops* AUI Publishing Co. pp. 237–246.
Phellips et al. (1988) *Corn & Corn Improvement* ASA monograph #18, 3rd edition G. F. Sprague editor, pp. 345–349 & 356–357.
Sass, (1977) *Corn & Corn Improvement* ASA monograph. #18 2nd edition. pp. 89–110.
Troyer et al. (1985) Crop Science vol. 25. pp. 695–697.

*Primary Examiner*—Gary Benzion
*Attorney, Agent, or Firm*—Pioneer Hi-Bred International, Inc.

[57] ABSTRACT

According to the invention, there is provided an inbred corn line, designated PHR61. This invention thus relates to the plants and seeds of inbred corn line PHR61 and to methods for producing a corn plant produced by crossing the inbred line PHR61 with itself or with another corn plant. This invention further relates to hybrid corn seeds and plants produced by crossing the inbred line PHR61 with another corn line or plant.

6 Claims, No Drawings

INBRED CORN LINE PHR61

CROSS REFERENCE TO RELATED APPLICATION

This is a continuation-in-part of prior application Ser. No. 07/649,800, filed Feb. 1, 1991, now abandoned.

FIELD OF THE INVENTION

This invention is in the field of corn breeding, specifically relating to an inbred corn line designated PHR61.

BACKGROUND OF THE INVENTION

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (*Zea mays L.*) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced:

$F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which has a genotype which complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, each breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

SUMMARY OF THE INVENTION

According to the invention, there is provided a novel inbred corn line, designated PHR61. This invention thus relates to the seeds of inbred corn line PHR61, to the plants of inbred corn line PHR61, and to methods for producing a corn plant produced by crossing the inbred line PHR61 with itself or another corn line. This invention further relates to hybrid corn seeds and plants produced by crossing the inbred line PHR61 with another corn line.

DEFINITIONS

In the description and examples that follow, a number of terms are used herein. In order to provide a clear and consistent understanding of the specification and claims, including the scope to be given such terms, the following definitions are provided:

BAR PLT = BARREN PLANTS. This is the percent of plants per plot that were not barren (lack ears).

BRT STK = BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR = YIELD (BUSHELS/ACRE). Actual yield of the grain at harvest adjusted to 15.5% moisture. ABS is in absolute terms and % MN is percent of the mean for the experiments in which the inbred or hybrid was grown.

DRP EAR = DROPPED EARS. This is a measure of the number of dropped ears per plot and represents the percentage of plants that did not drop ears prior to harvest.

EAR HT = EAR HEIGHT. The ear height is a measure from the ground to the top developed ear node attachment and is measured in inches.

EAR SZ = EAR SIZE. A 1 to 9 visual rating of ear size. The higher the rating the larger the ear size.

EST CNT = EARLY STAND COUNT. This is a measure of the stand establishment in the spring and represents the number of plants that emerge on a per plot basis for the inbred or hybrid.

GDU SHD = GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK = GDU TO SILK. The number of growing degree units required for an inbred line or hybrid to have approximately 50 percent of the plants with silk emergence from time of planting. Growing degree units are calculated by the Barger Method as given in GDU SHD definition.

GRN APP = GRAIN APPEARANCE. This is a 1 to 9 rating for the general appearance of the shelled grain as it is harvested based on such factors as the color of the harvested grain, any mold on the grain, and any cracked grain. High scores indicate good grain quality.

MST = HARVEST MOISTURE. The moisture is the actual percentage moisture of the grain at harvest.

PLT HT = PLANT HEIGHT. This is a measure of the height of the plant from the ground to the tip of the tassel in inches.

POL SC = POLLEN SCORE. A 1 to 9 visual rating indicating the amount of pollen shed. The higher the score the more pollen shed.

POL WT = POLLEN WEIGHT. This is calculated by dry weight of tassels collected as shedding commences minus dry weight from similar tassels harvested after shedding is complete. % MN is percent of the mean for the experiments in which the inbred or hybrid was grown.

PRM = PREDICTED RM. This trait, predicted relative maturity (RM), is based on the harvest moisture of the grain. The relative maturity rating is based on a known set of checks and utilizes standard linear regression analyses and is referred to as the Minnesota Relative Maturity Rating System.

RT LDG = ROOT LODGING. Root lodging is the percentage of plants that do not root lodge; plants that lean from the vertical axis at an approximately 30° angle or greater would be counted as root lodged.

SCT GRN = SCATTER GRAIN. A 1 to 9 visual rating indicating the amount of scatter grain (lack of pollination or kernel abortion) on the ear. The higher the score the less scatter grain.

SDG VGR = SEEDLING VIGOR. This is the visual rating (1 to 9) of the amount of vegetative growth after emergence at the seedling stage (approximately five leaves). A higher score indicates better vigor.

SEL IND = SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN = STAY GREEN. Stay green is the measure of plant health near the time of black layer formation (physiological maturity). A high score indicates better late-season plant health.

STK CNT = NUMBER OF PLANTS. This is the final stand or number of plants per plot.

STK LDG = STALK LODGING. This is the percentage of plants that did not stalk lodge (stalk breakage) as measured by either natural lodging or pushing the stalks and determining the percentage of plants that break below the ear.

TAS BLS = TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ = TASSEL SIZE. A 1 to 9 visual rating was used to indicate the relative size of the tassel. The higher the rating the larger the tassel.

TAS WT = TASSEL WEIGHT. This is the average weight of a tassel (grams) just prior to pollen shed.

TEX EAR = EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER = TILLERS. A count of the number of tillers per plot that could possibly shed pollen was taken. Data is given as percentage of tillers: number of tillers per plot divided by number of plants per plot.

TST WT = TEST WEIGHT UNADJUSTED. The measure of the weight of the grain in pounds for a given volume (bushel).

TST WTA = TEST WEIGHT ADJUSTED. The measure of the weight of the grain in pounds for a given volume (bushel) adjusted for percent moisture.

YLD = YIELD. It is the same as BU ACR ABS.

YLD SC = YIELD SCORE. A 1 to 9 visual rating was used to give a relative rating for yield based on plot ear piles. The higher the rating the greater visual yield appearance.

MDM CPX = Maize Dwarf Mosaic Complex (MDMV-Maize Dwarf Mosaic Virus & MCDV = Maize Chlorotic Dwarf Virus): Visual rating (1–9 score) where a "1" is very susceptible and a "9" is very resistant.

SLF BLT = Southern Leaf Blight (*Bipolaris maydis, Helminthosporium maydis*): Visual rating (1–9 score) where a "1" is very susceptible and a "9" is very resistant.

NLF BLT = Northern Leaf Blight (*Exserohilum turcicum, H. turcicum*): Visual rating (1–9 score) where a "1" is very susceptible and a "9" is very resistant.

COM RST = Common Rust (*Puccinia sorghi*): Visual rating (1–9 score) where a "1" is very susceptible and a "9" is very resistant.

GLF SPT = Gray Leaf Spot (*Cercospora zeae-maydis*): Visual rating (1–9 score) where a "1" is very susceptible and a "9" is very resistant.

STW WLT = Stewart's Wilt (*Erwinia stewartii*): Visual rating (1–9 score) where a "1" is very susceptible and a "9" is very resistant.

HD SMT = Head Smut (*Spacelotheca reiliana*): Percentage of plants that did not have infection.

EAR MLD = General Ear Mold: Visual rating (1–9 score) where a "1" is very susceptible and a "9" is very resistant. This is based on overall rating for ear mold of mature ears without determining specific mold organism, and may not be predictive for a specific ear mold.

ECB DPE = Dropped ears due to European Corn Borer (*Ostrinia nubilalis*): Percentage of plants that did not drop ears under second brood corn borer infestation.

ECB 2SC = European Corn Borer Second Brood (*Ostrinia nubilalis*): Visual rating (1–9 score) of post flowering damage due to infestation by European Corn Borer. A "1" is very susceptible and a "9" is very resistant.

ECB 1LF = European Corn Borer First Brood (*Ostrinia nubilalis*): Visual rating (1–9 score) of pre-flowering leaf feeding by European Corn Borer. A "1" is very susceptible and a "9" is very resistant.

DETAILED DESCRIPTION OF THE INVENTION

Inbred corn line PHR61 is a yellow, dent corn inbred that is best used as a female in crosses for producing first generation F1 corn hybrids. PHR61 is best adapted to the North Central Region of the United States. The inbred can be used to produce hybrids from approximately 105–117 relative maturity based on the Minnesota Relative Maturity Rating System for harvest moisture of grain. PHR61 has consistent high hybrid yields for its grain moisture maturity. PHR61 has excellent stalks, stay green, and grain quality. It has hard textured grain, high test weight, and good stress resistance. PHR61 has high inbred kernel yields, but has small kernels and has almost no inbred tassel branches, therefore, it does not make a good male. In hybrid combinations, the ear is medium in height and it has good ear retention, but plants are tall. Inbred PHR61 provides hybrids which, although adapted to cool Northern climates, perform exceptionally well in warm growing seasons which occasionally occur in the Northern Corn Belt of the United States.

The inbred has shown uniformity and stability within the limits of environmental influence for all the traits as described in the Variety Description Information (Table 1) that follows. Most of the data in the Variety Description Information was collected at Johnston, Iowa. The inbred has been self-pollinated and ear-rowed a sufficient number of generations with careful attention paid to uniformity of plant type to ensure homozygousity and phenotypic stability. The line has been increased both by hand and in isolated fields with continued observation for uniformity. No variant traits have been observed or are expected in PHR61.

Inbred corn line PHR61, being substantially homozygous, can be reproduced by planting seeds of the line, growing the resulting corn plants under self-pollinating or sib-mating conditions with adequate isolation, and harvesting the resulting seed, using techniques familiar to the agricultural arts.

TABLE 1

VARIETY DESCRIPTION INFORMATION

INBRED=PHR61

| Type: Dent | Region Best Adapted: North Central |
|---|---|

A. Maturity: Average across maturity zones. Zone: 0
   Heat Unit Shed: 1470
   Heat Unit Silk: 1490
   No. Reps: 54

$$\text{HEAT UNITS} = \frac{[\text{Max. Temp.} (\leq 86° \text{F.}) + \text{Min. Temp} (\geq 50° \text{F.})]*}{2} - 50$$

*If maximum is greater than 86 degrees fahrenheit, then 86 is used and if minimum is less than 50, then 50 is used. Heat units accumulated daily and can not be less than 0.

B. Plant Characteristics:
   Plant height (to tassel tip): 244 cm
   Length of top ear internode: 12 cm
   Number of ears per stalk: Single
   Ear height (to base of top ear): 81 cm
   Number of tillers: None
   Cytoplasm type: Normal
C. Leaf:
   Color: Medium Green (WF9)
   Angle from Stalk: <30 degrees
   Marginal Waves: Few (WF9)
   Number of Leaves (mature plants): 18
   Sheath Pubescence: Light (W22)

Longitudinal Creases: Few (OH56A)
Length (Ear node leaf): 75 cm
Width (widest point, ear node leaf): 10 cm
D. Tassel:
  Number lateral branches: 1
  Branch Angle from central spike: >45 degrees
  Pollen Shed: Low based on Pollen Yield Test
  Peduncle Length (top leaf to basal branches): 20 cm
  Anther Color: Yellow
  Glume Color: Green
E. Ear (Husked Ear Data Except When Stated Otherwise):
  Length: 16 cm
  Weight: 112 gm
  Mid-point Diameter: 38 mm
  Silk Color: Green
  Husk Extension (Harvest stage): Medium (Barely covering ear)
  Husk Leaf: Short (<8 cm)
  Taper of Ear: Slight
  Position of Shank (dry husks): Upright
  Kernel Rows: Straight, Distinct Number =14
  Husk Color (fresh): Light Green
  Husk Color (dry): Buff
  Shank Length: 13 cm
  Shank (No. of internodes): 8
F. Kernel (Dried):
  Size (from ear mid-point)
  Length: 10 mm
  Width: 6 mm
  Thick: 4 mm
  Shape Grade (% rounds): < 20 (13 % medium round based on Parent Test Data)
  Pericarp Color: Colorless
  Aleurone Color: Homozygous Yellow
  Endosperm Color: Yellow
  Endosperm Type: Normal Starch
  Gm Wt/100 Seeds (unsized): 24 gm
G. Cob:
  Diameter at mid-point: 20 mm
  Strength: Strong
  Color: Red
H. Diseases:
  Corn Lethal Necrosis (MCMV=Maize Chlorotic Mottle Virus and MDMV=Maize Dwarf Mosaic Virus): Intermediate
  Maize Dwarf Mosaic Complex (MDMV & MCDV= Maize Dwarf Virus): Susceptible
  Anthracnose Stalk Rot (*C. graminicola*): Intermediate
  S. Leaf Blight (*B. maydis*): Intermediate
  N. Leaf Blight (*E. turcicum*): Intermediate
  Common Rust (*P. sorghi*): Intermediate
  Southern Rust (*P. polysora*): Susceptible
  Gray Leaf Spot (*C. zeae*): Susceptible
  Stewart's Wilt (*E. stewartii): Susceptible*
  Goss's Wilt (*C. nebraskense*): Resistant
  Fusarium Ear Mold (*F. moniliforme*): Resistant
I. Insects:
  European Corn Borer-1 Leaf Damage (Pre-flowering): Intermediate
  European Corn Borer-2 (Post-flowering): Intermediate
  The above descriptions are based on a scale of 1–9, 1 being highly susceptible, 9 being highly resistant.
  S (Susceptible): Would generally represent a score of 1–3.
  I (Intermediate): Would generally represent a score of 4–5.
  R (Resistant): Would generally represent a score of 6–7.
  H (Highly Resistant): Would generally represent a score of 8–9. Highly resistant does not imply the inbred is immune.
J. Variety Most Closely Resembling:

| Character | Inbred |
|---|---|
| Maturity | PHG39 |
| Usage | PHG39 |

PHG39 (PVP Certificate No. 8300115) is a Pioneer Hi-Bred International, Inc. proprietary inbred.

Data for Items B, C, D, E, F, and G are based primarily on a maximum of four reps from Johnston, Iowa grown in 1989 and 1990, plus description information from the maintaining station.

ELECTROPHORESIS RESULTS

Isozyme Genotypes for PHR61

Isozyme data were generated for inbred corn line PHR61 according to the procedures described in Stuber, C. W., Wendel, J. F., Goodman, M. M., and Smith, J. S.C., "Techniques and Scoring Procedures for Starch Gel Electrophoresis of Enzymes from Maize (*Zea mays L.*)", Technical Bulletin No. 286, North Carolina Agricultural Research Service, North Carolina State University, Raleigh, N.C. (1988).

The data in Table 2 compares PHR61 with its parents, G39 and PHG69.

TABLE 2

ELECTROPHORESIS RESULTS FOR PHR61 AND ITS PARENTS G39 AND PHG69

| LOCI | PHR61 | PARENTS | |
|---|---|---|---|
| | | G39 | PHG69 |
| ACP1 | 4 | 4 | 2 |
| ADH1 | 4 | 4 | 4 |
| CAT3 | 9 | 9 | 9 |
| DIA1 | 12 | 8 | 12 |
| GOT1 | 4 | 4 | 4 |
| GOT2 | 2 | 2 | 4 |
| GOT3 | 4 | 4 | 4 |
| IDH1 | 4 | 4 | 4 |
| IDH2 | 6 | 6 | 6 |
| MDH1 | 6 | 6 | 1 |
| MDH2 | 6 | 6 | 3.5 |
| MDH3 | 16 | 16 | 16 |
| MDH4 | 12 | 12 | 12 |
| MDH5 | 12 | 12 | 12 |
| MMM | 4 | 4 | 4 |
| PGM1 | 9 | 9 | 9 |
| PGM2 | 4 | 4 | 8 |
| PGD1 | 2 | 2 | 2 |
| PGD2 | 5 | 5 | 2.8 |
| PHI1 | 4 | 4 | 4 |

INDUSTRIAL APPLICABILITY

This invention also is directed to methods for producing a corn plant by crossing a first parent corn plant with a second parent corn plant wherein the first or second parent corn plant is an inbred corn plant from the line PHR61. Further, both first and second parent corn plants can come from the inbred corn line PHR61. Thus, any such methods using the inbred corn line PHR61 are part of this invention: selfing, backcrosses, hybrid production, crosses to populations, and the like. All plants produced using inbred corn line PHR61 as a parent are within the scope of this invention.

Advantageously, the inbred corn line is used in crosses with other, different, corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottsville, Va. 1982, at 367–372) and in Duncan, et al., "The Production of Callus Capable of Plant Regeneration from Immature Embryos of Numerous Zea Mays Genotypes," 165 *Planta* 322–332 (1985). Thus, another aspect of this invention is to provide cells which upon growth and differentiation produce the inbred line PHR61.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHR61, the plant produced from the inbred seed, the hybrid corn plant produced from the crossing of the inbred, hybrid seed, and various parts of the hybrid corn plant can be utilized for human food, livestock feed, and as a raw material in industry.

Example

INBRED AND HYBRID PERFORMANCE OF PHR61

In the examples that follow, the traits and characteristics of inbred corn line PHR61 are given as a line and in hybrid combination. The data collected on inbred corn line PHR61 is presented for the key characteristics and traits.

Table 3A compares PHR61 to one of its parents, G39. The results show PHR61 and G39 have similar harvest moisture, but PHR61 has higher yield and test weight. PHR61 and G39 have similar plant height, but PHR61 has lower ear placement and flowers (GDU Shed and GDU Silk) earlier. PHR61 has a significantly smaller tassel, but has better ear texture and grain appearance than G39. PHR61 has worse stay green, is more susceptible to stalk, and has more brittle stalks than G39. PHR61 has slightly more resistance to ear mold and Northern leaf blight, but is more susceptible to common rust and second brood European corn borer than G39.

Table 3B contains results comparing PHR61 to PHG69. PHG69 is the other parent of PHR61. PHR61 and PHG69 have similar test weight, but PHR61 has higher yield and grain harvest moisture. PHR61 is taller with higher ear placement and flowers (GDU Shed and GDU Silk) later than PHG69. PHR61 has better grain appearance, significantly better stay green, and better resistance to stalk and root lodging than PHG69.

Tables 3C through 3F compare PHR61 with other Pioneer proprietary inbreds with similar genetic backgrounds, similar usage and proven performance in the area where PHR61 is adapted.

The results in Table 3C show PHR61 has lower yield and grain harvest moisture, but higher test weight than PHK29. PHR61 is a slightly taller plant with lower ear placement and flowers (GDU Shed and GDU Silk) earlier compared to PHK29. PHR61 has better seedling vigor and higher early stand count than PHK29. The tassel size of PHR61 is significantly smaller than PHK29, but PHR61 has better ear texture and grain appearance. PHK29 has better stay green and root lodging resistance, but PHR61 has better stalk lodging resistance. PHR61 is more susceptible to Stewart's wilt and first brood European corn borer, but more resistant to Northern and Southern leaf blight than PHK29.

The results in Table 3D compare PHR61 to PHR47. The results show PHR61 has higher yield, grain harvest moisture, and test weight than PHR47. PHR61 is a taller inbred with higher ear placement and flowers (GDU Shed and GDU Silk) later than PHR47. PHR61 has a smaller tassel and is more susceptible to root lodging, but has better ear texture, grain appearance, stay green, and is more resistant to stalk lodging and has fewer brittle stalks than PHR47.

The results in Table 3E compare PHR61 to PHT10. The results show PHR61 is significantly higher yielding, has significantly lower moisture at grain harvest, and has significantly higher test weight than PHT10. PHR61 and PHT10 have similar ear height, but PHR61 is a taller inbred and flowers (GDU Shed and GDU Silk) earlier. PHR61 has significantly better seedling vigor, early stand count, and cold test than PHT10. PHR61 has small tassels, good ear texture and grain appearance, and fewer brittle stalks, but lower stay green and is more susceptible to stalk and root lodging than PHT10. PHR61 and PHT10 have similar disease and insect resistance, but PHR61 has better Northern leaf blight resistance and is more susceptible to Stewart's wilt.

Table 3F compares PHR61 to the public inbred B73. PHR61 has lower yield and grain harvest moisture, but significantly higher test weight than B73. PHR61 is shorter with lower ear placement and flowers (GDU Shed and GDU Silk) earlier than B73. Compared to B73, PHR61 has better seedling vigor, higher early stand count, and better cold test. PHR61 has small tassels and better textured ears and grain appearance than B73. The root lodging of PHR61 and B73 are similar, but PHR61 is more resistant to stalk lodging and has fewer brittle stalks. PHR61 has better ear mold, Northern leaf blight, and first brood European corn borer but is more susceptible to Stewart's wilt and second brood European corn borer resistance than B73.

Table 4 compares a PHR61 hybrid to Pioneer Brand Hybrid 3417. 3417 has a parent in common with the PHR61 hybrid other than PHR61. 3417 is adapted to much of the same area as the PHR61 hybrid. The PHR61 hybrid is slightly lower yielding and has lower grain harvest moisture, but has significantly better test weight than 3417. The PHR61 hybrid is taller with higher ear placement and flowers (GDU Shed) later than 3417. The grain appearance is better, but stay green poorer for the PHR61 hybrid compared to 3417. The PHR61 hybrid is more susceptible to stalk and root lodging, but has fewer brittle stalks than 3417.

TABLE 3A

PAIRED INBRED COMPARISON DATA
VARIETY #1 = PHR61
VARIETY #2 = G39
* = 10% SIG  + = 5% SIG  # = 1% SIG

|  | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | CLD TST ABS |
|---|---|---|---|---|---|---|---|---|---|---|---|---|
| TOTAL SUM | 1 | 70.4 | 113 | 5.2 | 18.3 | 5.6 | 95.1 | 82.0 | 29.5 | 5.3 | 33.7 | 84.8 |
|  | 2 | 49.6 | 73 | 4.8 | 18.9 | 6.3 | 85.3 | 81.9 | 32.5 | 5.4 | 33.3 | 87.2 |
|  | LOCS | 10 | 10 | 22 | 12 | 11 | 13 | 18 | 17 | 27 | 48 | 6 |
|  | DIFF | 20.8 | 40 | 0.5 | 0.6 | 0.6 | 9.8 | 0.0 | 3.1 | 0.2 | 0.4 | 2.3 |
|  | PROB | .050* | .020+ | .213 | .192 | .269 | .007# | .998 | .000# | .587 | .426 | .777 |

|  | VAR # | CLD TST % MN | DRP EAR ABS | TIL LER ABS | GDU SHD ABS | GDU SLK ABS | POL SC ABS | TAS SZ ABS | TEX EAR ABS | TST WT ABS | GRN APP ABS | SCT GRN ABS |
|---|---|---|---|---|---|---|---|---|---|---|---|---|
| TOTAL SUM | 1 | 100 | 100.0 | 1.0 | 1475 | 1487 | 3.4 | 2.4 | 7.7 | 61.0 | 7.4 | 6.7 |
|  | 2 | 104 | 99.5 | 0.6 | 1549 | 1573 | 5.2 | 5.7 | 6.3 | 56.9 | 6.2 | 5.3 |
|  | LOCS | 6 | 7 | 17 | 45 | 41 | 18 | 17 | 7 | 10 | 8 | 19 |
|  | DIFF | 4 | 0.5 | 0.5 | 73 | 86 | 1.8 | 3.3 | 1.4 | 4.1 | 1.2 | 1.4 |
|  | PROB | .717 | .231 | .497 | .000# | .000# | .001# | .000# | .016+ | .000# | .021+ | .001# |

|  | VAR # | STA GRN ABS | STK LDG ABS | RT LDG ABS | BRT STK ABS | COM RST ABS | EAR MLD ABS | NLF BLT ABS | STW WLT ABS | ECB 1LF ABS | ECB 2SC ABS |
|---|---|---|---|---|---|---|---|---|---|---|---|
| TOTAL SUM | 1 | 5.1 | 92.5 | 84.0 | 98.0 | 5.0 | 7.0 | 5.5 | 2.0 | 4.0 | 3.4 |
|  | 2 | 6.5 | 94.9 | 79.0 | 100.0 | 8.0 | 6.3 | 4.2 | 4.5 | 4.2 | 4.1 |
|  | LOCS | 16 | 7 | 8 | 1 | 1 | 16 | 6 | 2 | 17 | 10 |
|  | DIFF | 1.5 | 2.3 | 4.9 | 2.0 | 3.0 | 0.7 | 1.3 | 2.5 | 0.2 | 0.7 |
|  | PROB | .006# | .442 | .298 |  |  | .102 | .043+ | .500 | .522 | .236 |

TABLE 3B

PAIRED INBRED COMPARISON DATA
VARIETY #1 = PHR61
VARIETY #2 = PHG69
* = 10% SIG  + = 5% SIG  # = 1% SIG

|  | VAR # | BU ACR ABS | BU ACR % MN | YLD SC ABS | MST ABS | EAR SZ ABS | BAR PLT ABS | PLT HT ABS | EAR HT ABS | SDG VGR ABS |
|---|---|---|---|---|---|---|---|---|---|---|
| TOTAL SUM | 1 | 62.6 | 130 | 6.0 | 19.7 | 6.5 | 94.9 | 100.0 | 32.0 | 5.0 |
|  | 2 | 55.7 | 117 | 5.5 | 15.9 | 3.5 | 91.7 | 93.0 | 24.3 | 4.3 |
|  | LOCS | 3 | 3 | 2 | 3 | 2 | 4 | 2 | 2 | 5 |
|  | DIFF | 6.9 | 12 | 0.5 | 3.8 | 3.0 | 3.2 | 7.0 | 7.7 | 0.7 |
|  | PROB | .272 | .258 | .874 | .088* | .000# | .656 | .045+ | .085* | .135 |

|  | VAR # | EST CNT ABS | DRP EAR ABS | TIL LER ABS | GDU SHD ABS | GDU SLK ABS | POL SC ABS | TAS SZ ABS | TEX EAR ABS | TST WT ABS |
|---|---|---|---|---|---|---|---|---|---|---|

TABLE 3B-continued

PAIRED INBRED COMPARISON DATA
VARIETY #1 = PHR61
VARIETY #2 = PHG69
* = 10% SIG   + = 5% SIG   # = 1% SIG

| | | | | | | | | | | |
|---|---|---|---|---|---|---|---|---|---|---|
| TOTAL SUM | 1 | 35.6 | 100.0 | 0.0 | 1508 | 1510 | 3.0 | 3.0 | 9.0 | 60.8 |
| | 2 | 34.5 | 100.0 | 0.9 | 1355 | 1387 | 2.0 | 3.0 | 8.0 | 60.6 |
| | LOCS | 7 | 3 | 4 | 3 | 3 | 1 | 1 | 2 | 3 |
| | DIFF | 1.0 | 0.0 | 0.9 | 153 | 123 | 1.0 | 0.0 | 1.0 | 0.2 |
| | PROB | .731 | 1.00 | .188 | .043+ | .101 | | | .500 | .635 |

| | VAR # | GRN APP ABS | SCT GRN ABS | STA GRN ABS | STK LDG ABS | RT LDG ABS | BRT STK ABS | EAR MLD ABS | ECB 1LF ABS | ECB 2SC ABS |
|---|---|---|---|---|---|---|---|---|---|---|
| TOTAL SUM | 1 | 7.2 | 7.0 | 5.9 | 84.9 | 100.0 | | 9.0 | 5.0 | 2.0 |
| | 2 | 6.9 | 7.0 | 1.8 | 78.9 | 98.1 | | 9.0 | 3.0 | 1.0 |
| | LOCS | 3 | 2 | 4 | 3 | 3 | | 2 | 1 | 3 |
| | DIFF | 0.3 | 0.0 | 4.1 | 6.0 | 1.9 | | 0.0 | 2.0 | 1.0 |
| | PROB | .766 | .000# | .001# | .725 | .234 | 1.00 | | | .000# |

TABLE 3C

PAIRED INBRED COMPARISON DATA
VARIETY #1 = PHR61
VARIETY #2 = PHK29
* = 10% SIG   + = 5% SIG   # = 1% SIG

| | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS |
|---|---|---|---|---|---|---|---|---|---|---|---|
| TOTAL SUM | 1 | 60.2 | 104 | 5.1 | 19.0 | 5.2 | 90.0 | 81.4 | 30.4 | 5.4 | 40.3 |
| | 2 | 66.5 | 108 | 5.7 | 20.0 | 5.0 | 89.9 | 80.0 | 31.5 | 5.0 | 37.4 |
| | LOCS | 39 | 39 | 27 | 43 | 14 | 33 | 36 | 35 | 64 | 101 |
| | DIFF | 6.3 | 5 | 0.6 | 0.9 | 0.2 | 0.1 | 1.3 | 1.1 | 0.4 | 2.9 |
| | PROB | .108 | .455 | .088* | .011+ | .568 | .979 | .293 | .143 | .065* | .000# |

| | VAR # | CLD TST ABS | CLD TST % MN | DRP EAR ABS | TIL LER ABS | GDU SHD ABS | GDU SLK ABS | POL SC ABS | TAS BLS ABS | TAS SZ ABS | TEX EAR ABS |
|---|---|---|---|---|---|---|---|---|---|---|---|
| TOTAL SUM | 1 | 89.8 | 104 | 99.9 | 1.6 | 1474 | 1487 | 3.4 | 7.5 | 2.3 | 7.6 |
| | 2 | 88.7 | 103 | 99.3 | 2.6 | 1486 | 1523 | 5.6 | 9.0 | 5.1 | 6.2 |
| | LOCS | 18 | 18 | 29 | 35 | 86 | 75 | 31 | 2 | 24 | 10 |
| | DIFF | 1.1 | 1 | 0.5 | 1.0 | 12 | 35 | 2.2 | 1.5 | 2.9 | 1.4 |
| | PROB | .684 | .784 | .027+ | .373 | .017+ | .000# | .000# | .500 | .000# | .007# |

| | VAR # | TST WT ABS | GRN APP ABS | SCT GRN ABS | STA GRN ABS | STK LDG ABS | RT LDG ABS | BRT STK ABS | COM RST ABS | EAR MLD ABS | GLF SPT ABS |
|---|---|---|---|---|---|---|---|---|---|---|---|
| TOTAL SUM | 1 | 60.5 | 7.6 | 6.8 | 5.2 | 92.0 | 85.3 | 99.3 | 5.3 | 7.3 | 2.2 |
| | 2 | 57.2 | 6.8 | 6.5 | 6.6 | 88.6 | 98.8 | 96.1 | 6.0 | 7.5 | 2.9 |
| | LOCS | 39 | 29 | 24 | 31 | 32 | 19 | 3 | 4 | 21 | 13 |
| | DIFF | 3.3 | 0.8 | 0.3 | 1.4 | 3.5 | 13.5 | 3.2 | 0.8 | 0.2 | 0.7 |
| | PROB | .000# | .005# | .491 | .003# | .127 | .015+ | .364 | .058* | .584 | .003# |

| | VAR # | GOS WLT ABS | MDM CPX ABS | NLF BLT ABS | SLF BLT ABS | STW WLT ABS | ECB DPE ABS | ECB 1LF ABS | ECB 2SC ABS |
|---|---|---|---|---|---|---|---|---|---|
| TOTAL SUM | 1 | 6.0 | 2.8 | 5.2 | 5.0 | 2.5 | 98.9 | 3.7 | 4.3 |
| | 2 | 8.8 | 2.3 | 3.7 | 4.4 | 7.3 | 95.0 | 4.1 | 4.5 |
| | LOCS | 2 | 2 | 17 | 6 | 3 | 4 | 31 | 30 |
| | DIFF | 2.8 | 0.5 | 1.5 | 0.6 | 4.8 | 3.9 | 0.3 | 0.2 |
| | PROB | .500 | .000# | .034+ | .435 | .048+ | .313 | .184 | .280 |

TABLE 3D

PAIRED INBRED COMPARISON DATA
VARIETY #1 = PHR61
VARIETY #2 = PHR47
* = 10% SIG    + = 5% SIG    # = 1% SIG

| | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | CLD TST ABS |
|---|---|---|---|---|---|---|---|---|---|---|---|---|
| TOTAL SUM | 1 | 61.9 | 109 | 5.8 | 19.1 | 5.7 | 87.8 | 81.9 | 30.5 | 5.4 | 37.1 | 92.2 |
| | 2 | 56.3 | 98 | 5.4 | 18.8 | 5.4 | 83.2 | 75.7 | 29.4 | 5.1 | 34.9 | 84.3 |
| | LOCS | 33 | 33 | 21 | 35 | 12 | 26 | 30 | 29 | 54 | 77 | 11 |
| | DIFF | 5.6 | 11 | 0.4 | 0.2 | 0.3 | 4.6 | 6.2 | 1.2 | 0.3 | 2.1 | 7.9 |
| | PROB | .024+ | .023+ | .329 | .540 | .586 | .049+ | .000# | .122 | .176 | .000# | .007# |

| | VAR # | CLD TST % MN | DRP EAR ABS | TIL LER ABS | GDU SHD ABS | GDU SLK ABS | POL SC ABS | TAS SZ ABS | TEX EAR ABS | TST WT ABS | GRN APP ABS | SCT GRN ABS |
|---|---|---|---|---|---|---|---|---|---|---|---|---|
| TOTAL SUM | 1 | 107 | 99.9 | 2.0 | 1466 | 1475 | 3.5 | 2.3 | 8.3 | 60.6 | 7.6 | 7.2 |
| | 2 | 97 | 99.9 | 2.8 | 1434 | 1471 | 6.2 | 5.5 | 6.1 | 57.3 | 6.0 | 6.1 |
| | LOCS | 11 | 24 | 24 | 66 | 58 | 17 | 23 | 8 | 33 | 22 | 20 |
| | DIFF | 9 | 0.1 | 0.8 | 32 | 05 | 2.8 | 3.2 | 2.1 | 3.2 | 1.7 | 1.0 |
| | PROB | .008# | .340 | .607 | .000# | .490 | .000# | .000# | .015+ | .000# | .000# | .001# |

| | VAR # | STA GRN ABS | STK LDG ABS | RT LDG ABS | BRT STK ABS | COM RST ABS | EAR MLD ABS | NLF BLT ABS | ECB DPE ABS | ECB 1LF ABS | ECB 2SC ABS |
|---|---|---|---|---|---|---|---|---|---|---|---|
| TOTAL SUM | 1 | 6.1 | 95.2 | 88.8 | 99.3 | 5.3 | 7.3 | 6.0 | 99.6 | 4.1 | 4.6 |
| | 2 | 5.5 | 95.0 | 93.8 | 92.9 | 7.7 | 6.6 | 6.0 | 100.0 | 4.3 | 5.9 |
| | LOCS | 21 | 24 | 18 | 3 | 3 | 20 | 6 | 2 | 24 | 23 |
| | DIFF | 0.6 | 0.2 | 5.0 | 6.4 | 2.3 | 0.7 | 0.0 | 0.4 | 0.2 | 1.3 |
| | PROB | .115 | .885 | .210 | .185 | .073* | .095* | .000# | .500 | .477 | .001# |

TABLE 3E

PAIRED INBRED COMPARISON DATA
VARIETY #1 = PHR61
VARIETY #2 = PHT10
* = 10% SIG    + = 5% SIG    # = 1% SIG

| | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | CLD TST ABS | CLD TST % MN |
|---|---|---|---|---|---|---|---|---|---|---|---|---|---|
| TOTAL SUM | 1 | 61.1 | 104 | 4.9 | 19.1 | 5.0 | 91.6 | 80.1 | 30.4 | 5.6 | 41.6 | 89.0 | 105 |
| | 2 | 51.2 | 80 | 5.4 | 20.9 | 5.7 | 74.8 | 76.0 | 31.1 | 4.4 | 38.9 | 77.3 | 91 |
| | LOCS | 34 | 34 | 22 | 36 | 12 | 21 | 28 | 27 | 47 | 70 | 12 | 12 |
| | DIFF | 10.0 | 25 | 0.5 | 1.9 | 0.7 | 16.8 | 4.1 | 0.7 | 1.1 | 2.7 | 11.7 | 14 |
| | PROB | .004# | .002# | .186 | .000# | .104 | .002# | .000# | .317 | .000# | .000# | .006# | .007# |

| | VAR # | DRP EAR ABS | TIL LER ABS | GDU SHD ABS | GDU SLK ABS | POL SC ABS | TAS BLS ABS | TAS SZ ABS | TEX EAR ABS | TST WT ABS | GRN APP ABS | SCT GRN ABS | STA GRN ABS |
|---|---|---|---|---|---|---|---|---|---|---|---|---|---|
| TOTAL SUM | 1 | 99.9 | 2.0 | 1468 | 1485 | 3.3 | 7.5 | 2.2 | 7.6 | 60.6 | 7.8 | 6.8 | 4.9 |
| | 2 | 99.9 | 2.3 | 1511 | 1544 | 6.8 | 9.0 | 6.5 | 5.0 | 56.4 | 6.5 | 6.2 | 5.8 |
| | LOCS | 24 | 23 | 63 | 55 | 18 | 2 | 16 | 10 | 33 | 24 | 19 | 19 |
| | DIFF | 0.1 | 0.3 | 42 | 59 | 3.6 | 1.5 | 4.3 | 2.6 | 4.1 | 1.3 | 0.6 | 0.9 |
| | PROB | .390 | .784 | .000# | .000# | .000# | .500 | .000# | .000# | .000# | .000# | .050* | .087* |

| | VAR # | STK LDG ABS | RT LDG ABS | BRT STK ABS | COM RST ABS | EAR MLD ABS | GLF SPT ABS | NLF BLT ABS | STW WLT ABS | ECB DPE ABS | ECB 1LF ABS | ECB 2SC ABS |
|---|---|---|---|---|---|---|---|---|---|---|---|---|
| TOTAL SUM | 1 | 96.8 | 82.6 | 99.5 | 5.5 | 7.4 | 2.0 | 5.0 | 2.0 | 99.6 | 4.0 | 5.1 |
| | 2 | 97.4 | 97.9 | 97.2 | 4.0 | 7.4 | 3.0 | 3.8 | 3.5 | 100.0 | 4.5 | 5.3 |
| | LOCS | 24 | 16 | 4 | 2 | 14 | 1 | 4 | 2 | 2 | 17 | 18 |
| | DIFF | 0.6 | 15.3 | 2.3 | 1.5 | 0.1 | 1.0 | 1.3 | 1.5 | 0.4 | 0.5 | 0.3 |
| | PROB | .413 | .018+ | .261 | .205 | .880 | | .239 | .205 | .500 | .132 | .288 |

65

TABLE 3F

PAIRED INBRED COMPARISON DATA
VARIETY #1 = PHR61
VARIETY #2 = B73
* = 10% SIG   + = 5% SIG   # = 1% SIG

|  | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | CLD TST ABS | CLD TST % MN |
|---|---|---|---|---|---|---|---|---|---|---|---|---|---|
| TOTAL SUM | 1 | 68.1 | 116 | 5.2 | 17.3 | 5.6 | 90.9 | 81.7 | 28.2 | 5.2 | 39.5 | 89.8 | 104 |
|  | 2 | 76.4 | 120 | 6.6 | 20.4 | 6.0 | 88.6 | 84.1 | 34.2 | 4.9 | 37.4 | 85.6 | 100 |
|  | LOCS | 11 | 11 | 22 | 15 | 11 | 24 | 20 | 19 | 32 | 64 | 18 | 18 |
|  | DIFF | 8.3 | 4 | 1.4 | 3.0 | 0.4 | 2.3 | 2.4 | 6.0 | 0.2 | 2.0 | 4.2 | 5 |
|  | PROB | .337 | .755 | .001# | .000# | .492 | .471 | .059* | .000# | .285 | .002# | .104 | .133 |

|  | VAR # | DRP EAR ABS | TIL LER ABS | GDU SHD ABS | GDU SLK ABS | POL SC ABS | TAS BLS ABS | TAS SZ ABS | TEX EAR ABS | TST WT ABS | GRN APP ABS | SCT GRN ABS | STA GRN ABS |
|---|---|---|---|---|---|---|---|---|---|---|---|---|---|
| TOTAL SUM | 1 | 100.0 | 1.4 | 1480 | 1490 | 3.3 | 7.5 | 2.3 | 7.4 | 60.9 | 7.6 | 6.7 | 5.3 |
|  | 2 | 99.5 | 3.4 | 1525 | 1553 | 5.5 | 8.0 | 5.4 | 5.7 | 55.1 | 6.1 | 7.1 | 3.8 |
|  | LOCS | 8 | 27 | 59 | 56 | 27 | 2 | 18 | 7 | 11 | 9 | 20 | 19 |
|  | DIFF | 0.5 | 2.0 | 44 | 63 | 2.1 | 0.5 | 3.0 | 1.7 | 5.9 | 1.5 | 0.5 | 1.5 |
|  | PROB | .136 | .338 | .000# | .000# | .000# | .874 | .000# | .001# | .000# | .096* | .191 | .005# |

|  | VAR # | STK LDG ABS | RT LDG ABS | BRT STK ABS | COM RST ABS | EAR MLD ABS | NLF BLT ABS | STW WLT ABS | ECB DPE ABS | ECB 1LF ABS | ECB 2SC ABS |
|---|---|---|---|---|---|---|---|---|---|---|---|
| TOTAL SUM | 1 | 92.9 | 79.3 | 98.0 | 5.0 | 7.2 | 5.7 | 2.0 | 98.3 | 3.8 | 3.5 |
|  | 2 | 88.7 | 79.1 | 95.7 | 7.0 | 6.7 | 4.8 | 6.5 | 98.3 | 3.3 | 3.0 |
|  | LOCS | 8 | 9 | 1 | 2 | 16 | 7 | 2 | 2 | 22 | 17 |
|  | DIFF | 4.2 | 0.2 | 2.3 | 2.0 | 0.5 | 0.9 | 4.5 | 0.0 | 0.5 | 0.5 |
|  | PROB | .359 | .980 |  | .000# | .366 | .162 | .070* | .000# | .100 | .050* |

TABLE 4

PHR61 HYBRID COMPARED TO PIONEER BRAND HYBRID 3417
VARIETY #1 — PHR61 HYBRID
VARIETY #2 — 3417
* = 10% SIG   + = 5% SIG   # = 1% SIG

| YEAR |  | VAR # | BU ACR ABS | BU ACR % MN | MST ABS | PLT HT ABS | EAR HT ABS | SDG VGR ABS | EST CNT ABS | DRP EAR ABS |
|---|---|---|---|---|---|---|---|---|---|---|
| TOTAL SUM |  | 1 | 143.2 | 101 | 19.2 | 102.8 | 44.6 | 5.2 | 59.7 | 99.6 |
|  |  | 2 | 144.7 | 103 | 22.0 | 96.6 | 41.5 | 5.6 | 58.5 | 99.8 |
|  |  | LOCS | 241 | 241 | 241 | 107 | 107 | 122 | 164 | 157 |
|  |  | DIFF | 1.5 | 1 | 2.8 | 6.2 | 3.1 | 0.4 | 1.2 | 0.1 |
|  |  | PROB | .137 | .066* | .000# | .000# | .000# | .000# | .005# | .158 |

| YEAR |  | VAR # | GDU SHD ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM |  | 1 | 1378 | 57.0 | 6.7 | 5.1 | 92.0 | 96.6 | 99.3 |
|  |  | 2 | 1363 | 56.0 | 6.1 | 5.9 | 93.1 | 98.7 | 97.9 |
|  |  | LOCS | 78 | 238 | 168 | 113 | 233 | 93 | 10 |
|  |  | DIFF | 15 | 1.0 | 0.5 | 0.8 | 1.0 | 2.1 | 1.4 |
|  |  | PROB | 000# | .000# | .000# | .000# | .036+ | .003# | .048+ |

Deposits

Applicant has made a deposit of at least 2500 seeds of PHR61 with the American Type Culture Collection (ATCC), Rockville, Md. 20852 USA, ATCC Deposit No. 97123. The seeds deposited with the ATCC are taken from the same deposit maintained by Pioneer Hi-Bred International, Inc., 700 Capital Square, 400 Locust Street, Des Moines, Iowa 50309 since prior to the filing date of this application. This deposit of the inbred corn line PHR61 will be maintained in the ATCC depository, which is a public depository, for a period of 30 years, or 5 years after the most recent request, or for the effective life of the patent, whichever is longer, and will be replenished or replaced if it is depleted or becomes nonviable during that period. Additionally, Applicant has satisfied all the requirements of 37 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

What is claimed is:

1. Inbred corn seed designated PHR61 and having ATCC Accession No. 97123.

2. A corn plant and its parts produced by the seed of claim 1.

3. An inbred corn plant having all the physiological and morphological characteristics of the plant generated from the seed of claim 1.

4. A corn plant regenerated from a culture of tissue taken from a plant according to claim 2 and selected from the group consisting of meristematic tissue, immature embryos, microspores, protoplasts, and pollen.

5. A process to produce a hybrid corn seed which gives rise to a hybrid corn plant having alleles which, when expressed, contribute to hybrids which are adapted to the northern corn belt and which also perform well during warm growing seasons that occasionally occur in the northern corn belt compared to similarly adapted hybrids, comprising the steps of:

(a) planting, in pollinating proximity, seed of corn inbred line PHR61 having ATCC accession no. and another inbred line, not PHR61;

(b) cultivating corn plants resulting from said planting, said corn plants having a male and female reproductive system;

(c) inactivating the male reproductive system prior to pollination of the plants of either the female inbred line;

(d) allowing natural cross pollinating to occur between the inbred lines; and (e) harvesting seeds produced on said inactivated plants of the inbred line.

6. $F_1$ hybrid corn seed and plants therefrom produced by crossing inbred corn plant PHR61 having ATCC No.—with another corn plant that is not PHR61.

* * * * *